United States Patent [19]
Sirges et al.

[11] Patent Number: 5,739,360
[45] Date of Patent: Apr. 14, 1998

[54] INTERMEDIATES FOR THE SYNTHESIS OF BISPHOSPHINE COMPOUNDS

[75] Inventors: Wolfram Sirges, Düsseldorf; Christian Laue, Monheim; Dieter Arlt, Köln; Rolf Grosser, Leverkusen, all of Germany

[73] Assignee: Bayer Aktiengesellschaft, Leverkusen, Germany

[21] Appl. No.: 714,747

[22] Filed: Sep. 16, 1996

[30] Foreign Application Priority Data

Sep. 22, 1995 [DE] Germany ............. 195 35 243.2

[51] Int. Cl.6 .................................. C07D 307/91
[52] U.S. Cl. ....................................... 549/460
[58] Field of Search ................................. 549/460

[56] References Cited

U.S. PATENT DOCUMENTS

| | | |
|---|---|---|
| 5,274,167 | 12/1993 | Lange et al. . |
| 5,302,738 | 4/1994 | Foricher et al. . |
| 5,510,503 | 4/1996 | Laue et al. . |

FOREIGN PATENT DOCUMENTS

| | | |
|---|---|---|
| 643065 | 3/1995 | European Pat. Off. . |
| 4318013 | 12/1994 | Germany . |
| 9216536 | 10/1992 | WIPO . |

*Primary Examiner*—C. Warren Ivy
*Assistant Examiner*—Jean F. Vollano
*Attorney, Agent, or Firm*—Sprung Kramer Schaefer & Briscoe

[57] ABSTRACT

The invention relates to novel bisphosphonates and to processes for their preparation and for their resolution into the enantiomers. The bisphosphonates according to the invention are valuable intermediates for the preparation of bisphosphine compounds, especially chiral bisphosphine ligands. These in turn are constituents of transition metal complexes which are used as catalysts inter alia in asymmetric hydrogenation.

The novel bisphosphonates have the general formula (I)

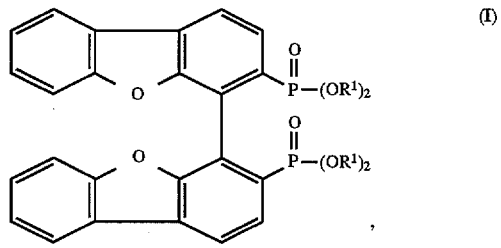

in which $R^1$ is linear or branched alkyl having up to 6 carbon atoms, aryl or aralkyl, each of which can optionally be substituted, or two radicals $R^1$ together are a bridging hydrocarbon radical having up to 6 carbon atoms, and can exist in the form of their racemates or as enantiomers.

7 Claims, No Drawings

INTERMEDIATES FOR THE SYNTHESIS OF BISPHOSPHINE COMPOUNDS

The invention relates to novel bisphosphonates and to processes for their preparation and for their resolution into the enantiomers. The bisphosphonates according to the invention are valuable intermediates for the preparation of bisphosphine compounds, especially chiral bisphosphine ligands. These in turn are constituents of transition metal complexes which are used as catalysts inter alia in asymmetric hydrogenation.

EP-A 0 643 065 has disclosed enantiomerically pure bisphosphines, processes for their preparation and their use in metal complexes as catalysts for asymmetric hydrogenations.

In this process, the necessary resolution into the enantiomers is effected by chromatography at the bisphosphine oxide stage.

Surprisingly, it has now been found that bisphosphonates (I) are considerably easier to resolve into the enantiomers than the known bisphosphine oxides.

The invention therefore relates to bisphosphonates of the general formula (I)

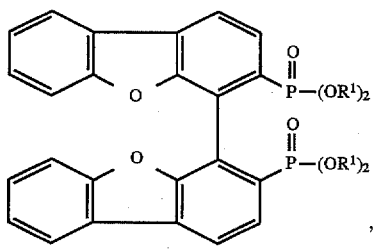

in which $R^1$ is linear or branched alkyl having up to 6 carbon atoms, aryl or aralkyl, each of which can optionally be substituted, or two radicals $R^1$ together are a bridging hydrocarbon radical having up to 6 carbon atoms, in the form of their racemates or as enantiomers.

Preferred compounds of the general formula (I) are those in which $R^1$ is an alkyl group having up to 4 C atoms, particularly preferably ethyl.

The invention further relates to a process for the preparation of compounds of the general formula (I) wherein halogen compounds of the general formula (II)

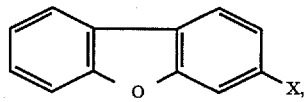

in which

X is halogen, especially bromine, are reacted with a compound $P(OR^1)_3$, in which $R^1$ is as defined above, in the presence of a suitable catalyst, especially palladium (II) or nickel(II) halides, e.g. $PdCl_2$ or $NiBr_2$, and in solvents, to give compounds of the general formula (III)

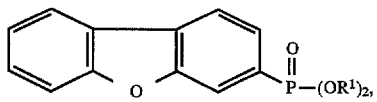

in which $R^1$ is as defined above.

Ortho-lithiation, for example with a lithium amide like lithium diisopropylamide in tetrahydrofuran, followed by halogenation, preferably iodination, for example with molecular iodine, ICl or IBr, converts the compounds of the formula (III) to compounds of the formula (IV)

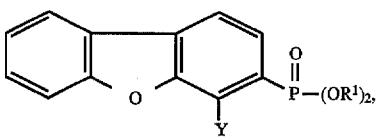

in which $R^1$ is as defined above and

Y is halogen, preferably iodine.

Both reactions are carried out at temperatures below 0° C., preferably in the range 0° C. to −100° C.

Racemic compounds of the formula (I)

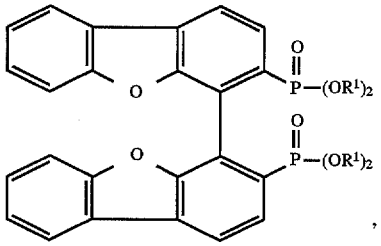

can be prepared from the compounds of the formula (IV) by coupling reactions known per se, e.g. by means of an Ullmann coupling, the preferred procedure being to heat compounds of the formula (IV) with copper powder at temperatures of 80° C. to 250° C., optionally in an inert organic solvent, e.g. dimethylformamide or nitromethane.

The invention further relates to the novel intermediates of the general formulae (III). and (IV).

It has now been found that the enantiomers of the formula (I) can be separated on chiral stationary phases, e.g. polymers of optically active (meth)acrylic acid derivatives, cellulose derivative phases (e.g. esters and carbamates) or cellulose triacetate phases. It is preferable to use optically active polymers of optically active (meth)acrylic acid derivatives as bead polymers or in a form bound to silica gel, as described in US-A-5 274 167. Particularly preferred bead polymers are those of N-(meth)acryloyl-L-alanine-L-menthylamide and particularly preferred silica gel phases are those of N-(meth)acryloyl-L-leucine-2,4-dimethyl-3-pentylamide.

The eluents used for the resolution of the racemates are conventional organic solvents or solvent mixtures. The following may be mentioned as examples: hydrocarbons such as benzene, toluene or xylene, ethers such as diethyl ether, dioxane or tetrahydrofuran, halogenohydrocarbons such as di- or tri-chloromethane, acetone, acetonitrile, alcohols such as ethanol or propanol, ethyl acetate or mixtures of said solvents. Toluene/tetrahydrofuran mixtures and toluene/dioxane mixtures have proved particularly suitable.

The separation of the enantiomers can be described by the separation factor α. The separation factor α, also known as the enantioselectivity value, is defined by the following formula:

$$\alpha = \frac{k'_2}{k'_1}$$
Separation factor $$k'_{1(2)} = \frac{t_{1(2)} - t_0}{t_0}$$
Capacity ratio $t_0$=Dead time of the column $t_{1(2)}$=Retention time of enantiomer 1 eluted first or of enantiomer 2 eluted afterwards.

α values of more than 2 can be achieved with the bisphosphonates according to the invention. By contrast, the separation factor a of the bisphosphine oxides in the process described in EP-A 0 643 065 has values of around 1.3. A further distinction is the markedly higher solubility of the bisphosphonates according to the invention compared with the bisphosphine oxides.

By virtue of these unexpectedly favourable properties, the bisphosphonates of the general formula (I) according to the invention are suitable as key compounds for the synthesis of chiral bisphosphine ligands. These can be prepared e.g. by converting the compounds of the formula (I) by conventional methods to the phosphonic acid halides and using the latter to prepare bisphosphine oxide compounds, for example by reaction with Grignard compounds. By following the instructions in EP-A 0 643 065, said bisphosphine oxides can be reduced to bisphosphine ligands, which in turn are valuable for the preparation of chiral transition metal complexes as stereoselective catalysts.

EXAMPLES

1. Preparatory Example

Synthesis of bis-diethyl (bis-4,4'-dibenzofuran-3,3'-yl)-phosphonate

1a) Diethyl (dibenzofuran-3-yl)-phosphonate (III)

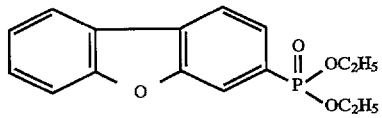

A mixture of 100 g (0.34 mol) of 3-bromo-dibenzofuran, 1.2 g (6 mmol) of palladium dichloride and 68 g (0.41 mol) of triethyl phosphite was heated to 160° C., with stirring. The ethyl bromide formed was removed from the reaction mixture with a gentle stream of nitrogen. Three times 68 g of triethyl phosphite were added after 1-hour intervals and the reaction mixture was then kept at 160° C. overnight. The excess triethyl phosphite was removed under high vacuum and the product was purified by column chromatography (cyclohexane/ethyl acetate 1:1).

Yield: 95 g (92%)
M.p.: 58 to 60° C.

1b) Diethyl (4-iodo-dibenzofuran-3-yl)-phosphonate (IV)

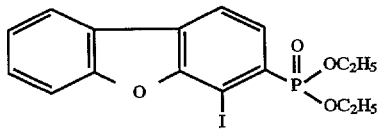

25 g (82 mmol) of diethyl (dibenzofuran-3-yl)-phosphonate were dissolved in 1.5 l of anhydrous THF and the solution was cooled to −78° C. under inert gas. A solution of 82 mmol of lithium diisopropylamide in THF, previously freshly prepared from 8.3 g (82 mmol) of diisopropylamide and 82 mmol of n-butyllithium in THF, was added dropwise at this temperature. The mixture was stirred for a further 10 min and a solution of 20.8 g (82 mmol) of iodine in 400 ml of anhydrous THF was then added dropwise in such a way that the temperature did not exceed −70° C. After stirring for a further 10 min, the mixture was hydrolysed with saturated ammonium chloride solution and the phases were separated. The Organic phase was washed with sodium sulphite solution and ammonium chloride solution and dried over $MgSO_4$. Evaporation of the solvent gave 33.9 g of a light brown solid.

Yield: 33.9 g (95%) with a purity of 97% (GC).

1c) Racemic bis-diethyl (bis-4,4'-dibenzofuran-3,3'-yl)-phosphonate (I)

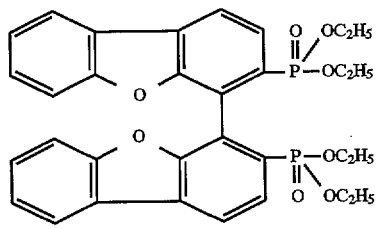

Under an inert gas atmosphere, 33 g (76 mmol) of diethyl (2-iodo-dibenzofuran-3-yl)-phosphonate were dissolved in 500 ml of anhydrous N,N-diethylformamide and 20 g (0.3 mol) of copper powder were added. The dark brown suspension was heated at 140° C. for 20 h under a nitrogen atmosphere, with vigorous stirring. The hot reaction solution was filtered on Célite and the filter was rinsed with 200 ml of methylene chloride. The reaction mixture was subsequently evaporated to dryness under vacuum. The brown oil obtained was extracted by stirring with tert-butyl methyl ether and the slightly brownish-coloured solid was filtered off with suction.

M.p.: 182° C.

Yield: 17.3 g (75%)

2. Example

Resolution of the racemate by chromatography 0.5 g of racemic bis-diethyl (bis-4,4'-dibenzofuran-3,3'-yl)-phosphonate, dissolved in 24 ml of THF and 16 ml of n-heptane, was applied to a steel column (63 mm, length 50 cm) containing a silica gel phase of N-(meth)acryloyl-L-leucine-2,4-dimethyl-3-pentylamide. Elution was carried out with n-heptane/THF (3:2; v/v) at a flow rate of 100 ml/min. The (+)-enantiomer was obtained first after 21.2 min and the (−)-enantiomer was eluted after 28.0 min. After the enantiomeric purity had been checked by analysis, the fractionated eluates were combined. Conventional working-up gave 0.22 g of the (+)-enantiomer, eluted first, and 0.2 g of the corresponding (−)-enantiomer.

R(+)-bis-diethyl (bis-4,4'-dibenzofuran-3,3'-yl)-phosphonate $[\alpha]_D$=+72° (c=1, $CHCl_3$)

S(−)-bis-diethyl (bis-4,4'-dibenzofuran-3,3'-yl)-phosphonate $[\alpha]_D$=−72° (c=1, $CHCl_3$)

3. Application Example

Synthesis of (+)-(bis-4,4'-dibenzofuran-3,3'-yl)-bis (diphenylphosphine oxide)

3a) (+)-(Bis-4,4'-dibenzofuran-3,3'-yl)bis(phosphonic acid dichloride)

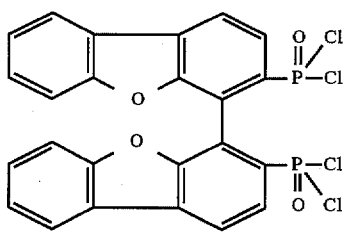

6 g (10 mmol) of (+)-bis-diethyl (bis-2,2'-dibenzofuran-3,3'-yl)-phosphonate were dissolved in 7.3 ml (100 mmol) of thionyl chloride and 0.8 ml of dry diethylformamide and the solution was refluxed for 4 h under inert gas. The excess thionyl chloride was then distilled off and the residue was dried under vacuum. The brownish viscous oil was taken up with methylene chloride and filtered. The product was precipitated with diethyl ether and the precipitate formed was filtered off with suction and dried.

Yield: 5.1 g (89%)

M.p.: >250° C.

3b) (+)-(Bis-4,4'-dibenzofuran-3,3'-yl)-bis (diphenylphosphine oxide)

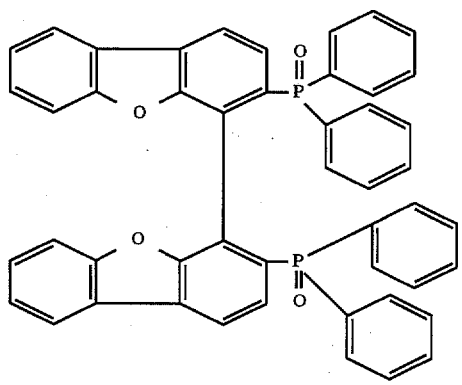

5 g (9 mmol) of (+)-(bis-2,.2'-dibenzofuran-3,3'-yl)bis (phosphonic acid dichloride) were dissolved in 400 ml of dry THF and the solution was cooled to −78° C. under inert gas. 30 ml of a 3M solution of phenylmagnesium bromide in diethyl ether were added at this temperature. The mixture was stirred for 30 min and then allowed to warm up to room temperature. Excess phenylmagnesium bromide was quenched with saturated ammonium chloride solution and the phases were separated. The organic phase was washed with saturated sodium chloride solution and dried over MgSO$_4$. After evaporation of the solvent, the residue was taken up with methylene chloride, and ethyl acetate was added to the solution. The methylene chloride was distilled off and the precipitate formed was filtered off with suction and dried.

Yield: 4.6 g (70%)

M.p.: 270° to 280° C.

Following the instructions in EP-A 0 643 065, the phosphine oxides obtainable as described above can be used to prepare chiral bisphosphines and hence chiral transition metal catalysts.

We claim:

1. Bisphosphonates of the general formula (I)

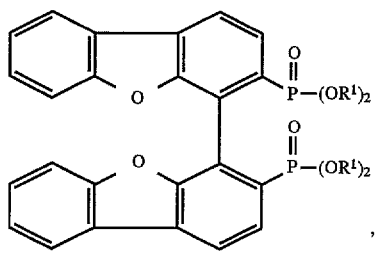

(I)

in which

R$^1$ is linear or branched alkyl having up to 6 carbon atoms, aryl or aralkyl, each of which can optionally be substituted, or two radicals R$^1$ together are a bridging hydrocarbon radical having up to 6 carbon atoms, in the form of their racemates or as enantiomers.

2. Bisphosphonates of the general formula (I) according to claim 1, characterized in that R$^1$ is linear or branched alkyl having up to 4 carbon atoms, in the form of their racemates or as enantiomers.

3. Process for the preparation of compounds of the general formula (I)

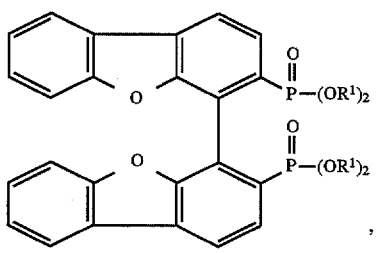

(I)

in which

R$^1$ is linear or branched alkyl having up to 6 carbon atoms, aryl or aralkyl, each of which can optionally be substituted, or two radicals R$^1$ together are a bridging hydrocarbon radical having up to 6 carbon atoms, characterized in that compounds of the general formula (II)

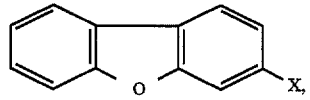

(II)

in which

X is halogen, are reacted with a compound P(OR$^1$)$_3$, in which R$^1$ is as defined above, optionally in the presence of a catalyst and in solvents, to give compounds of the general formula (III)

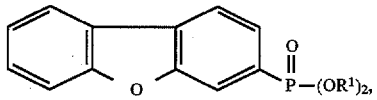

(III)

in which R$^1$ is as defined above, these are convened by ortho-lithiation and subsequent halogenation to compounds of the general formula (IV)

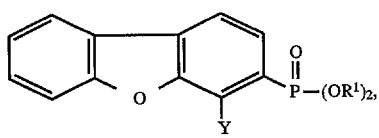
(IV)

in which
R¹ is as defined above and
Y is halogen, and racemic compounds of the general formula (I) are prepared from the latter by means of coupling reactions known per se and are resolved into the enantiomers by chromatography.

4. Process according to claim 3, characterized in that the chromatographic separation of the enantiomers is carried out on chiral stationary phases.

5. Process according to claim 4, characterized in that the chiral stationary phase comprises an optically active polymer of optically active (meth)acrylic acid derivatives, cellulose derivative phases or cellulose triacetate phases.

6. Preparation of chiral bisphosphine compounds wherein the compounds of formula (I) according to claim 1 are employed as intermediates.

7. Preparation of stereoselective transition metal catalysts wherein the compounds of formula (I) according to claim 1 are employed as intermediates.

* * * * *